United States Patent [19]

Nagel

[11] Patent Number: 5,371,555
[45] Date of Patent: Dec. 6, 1994

[54] PRESCRIPTION GOGGLES

[76] Inventor: Randy Nagel, 357 Sandy Point Ct. NE., Rochester, Minn. 55906

[21] Appl. No.: 18,896

[22] Filed: Feb. 17, 1993

[51] Int. Cl.$^5$ .......................... G02C 7/08; A61F 9/02
[52] U.S. Cl. ................................ 351/57; 351/155; 351/158; 2/444
[58] Field of Search ............. 351/57 OR, 44, 83, 90, 351/103, 110, 155, 156, 158; 2/444, 443

[56] References Cited

U.S. PATENT DOCUMENTS

| | | |
|---|---|---|
| 2,274,791 | 3/1942 | Huggins ............................ 2/444 |
| 2,396,207 | 3/1946 | Schutz et al. .................. 351/158 |
| 3,944,345 | 3/1976 | Decorato ......................... 351/57 |
| 4,550,989 | 11/1985 | Hafner ........................... 351/103 |
| 4,563,065 | 1/1986 | Kreissl ........................... 351/57 |
| 4,810,080 | 3/1989 | Grendol et al. ................ 351/158 |
| 4,930,163 | 6/1990 | King ................................ 2/444 |
| 5,007,727 | 4/1991 | Kahaney et al. ................ 351/57 |
| 5,106,178 | 4/1992 | Akiyoshi ......................... 351/57 |
| 5,137,341 | 8/1992 | Gendol et al. ................... 2/443 |

FOREIGN PATENT DOCUMENTS

| | | |
|---|---|---|
| 2718679 | 11/1978 | Germany ........................ 351/158 |
| 0159678 | 3/1983 | Germany .......................... 2/444 |
| 270685 | 9/1950 | Switzerland ..................... 351/44 |

OTHER PUBLICATIONS

Advertisement for SUPERSEER Goggles, No Date Available.
Advertisement for UVEX Prescription Goggles, No Date Available.
Advertisement for BOLLÉ Prescription Ski Goggles, No Date Available.
Advertisement for PRO-VUE Prescription Goggle Lens Systems, No Date Available.

*Primary Examiner*—Richard A. Bertsch
*Assistant Examiner*—Howard R. Richman
*Attorney, Agent, or Firm*—Kinney & Lange

[57] ABSTRACT

A goggles assembly comprising a pair of goggles having an outer lens, an inner lens attached to the goggles, and a pair of corrective lenses. The inner lens is held spaced from the outer lens by a pair of pegs which are inserted through both the outer and inner lenses. A groove is formed in an outer edge of each corrective lens and each corrective lens is press-fitted into an opening cut in the inner lens. The corrective lenses can be removed from the inner lens by pressing them out of the openings.

16 Claims, 3 Drawing Sheets

PRESCRIPTION GOGGLES

BACKGROUND OF THE INVENTION

The present invention relates to the use of goggles in active sports such as skiing and motocross and, in particular, to goggles in which corrective lenses may be mounted.

In many sports and other activities, there is a need for participants to wear protective eye wear or goggles. For those persons who normally wear corrective eyeglasses, a choice must often be made between protecting their eyes through the use of goggles and using corrective eyeglasses to see clearly while participating in an activity. There is therefore a need for goggles in which corrective lenses can be mounted.

Previous attempts to provide such a device include mounting an ordinary eyeglass frame holding corrective lenses in a protective mask or in other protective eye wear. Assemblies of this kind have the drawback of being bulky and heavy, and the corrective lenses can shift in position during use, interfering with the user. Other such devices simply use an adhesive to attach corrective lenses to a lens in a pair of goggles. Such devices, while not as bulky, do not allow for the corrective lenses to be replaced without replacing the lens to which they are attached.

There is therefore a need for goggles in which corrective lenses can be mounted in a manner that does not interfere with or burden the user. Additionally, it would be desirable to have the corrective lenses mounted in a manner that permits them to be easily removed from the goggles and also protects them from becoming scratched or otherwise damaged during use of the goggles.

SUMMARY OF THE INVENTION

The present invention provides a protective goggles assembly in which corrective lenses are mounted in a position which protects them from scratches and other damage that may occur during use and in a manner which enables them to be easily removed from the protective goggles assembly.

The protective goggles assembly comprises a pair of goggles having an outer lens, an inner lens attached to the goggles, and a pair of corrective lenses mounted in the inner lens. The inner lens is attached to the goggles behind the outer lens through the use of two pegs which are inserted through holes drilled in both the inner and outer lenses.

A pair of openings is formed in the inner lens for receiving the corrective lenses while a groove is formed in an outer edge of each corrective lens. The corrective lenses are mounted in the inner lens by press-fitting them into the openings in the inner lens such that the edges of the inner lens formed around each of the openings snap into the grooves of the corrective lenses, holding them in place. The goggles can be any one of a variety of types of goggles, such as those made for motocross or skiing.

The mounting of the corrective lenses in the inner lens prevents them from being scratched or otherwise damaged during use of the goggles. When the outer lens of the goggles becomes scratched, it can be easily replaced at a minimal cost. The corrective lenses can be easily removed from the openings in the inner lens so that they may be replaced if necessary.

DETAILED DESCRIPTION OF THE PREFERRED EMBODIMENTS

Figure 1:
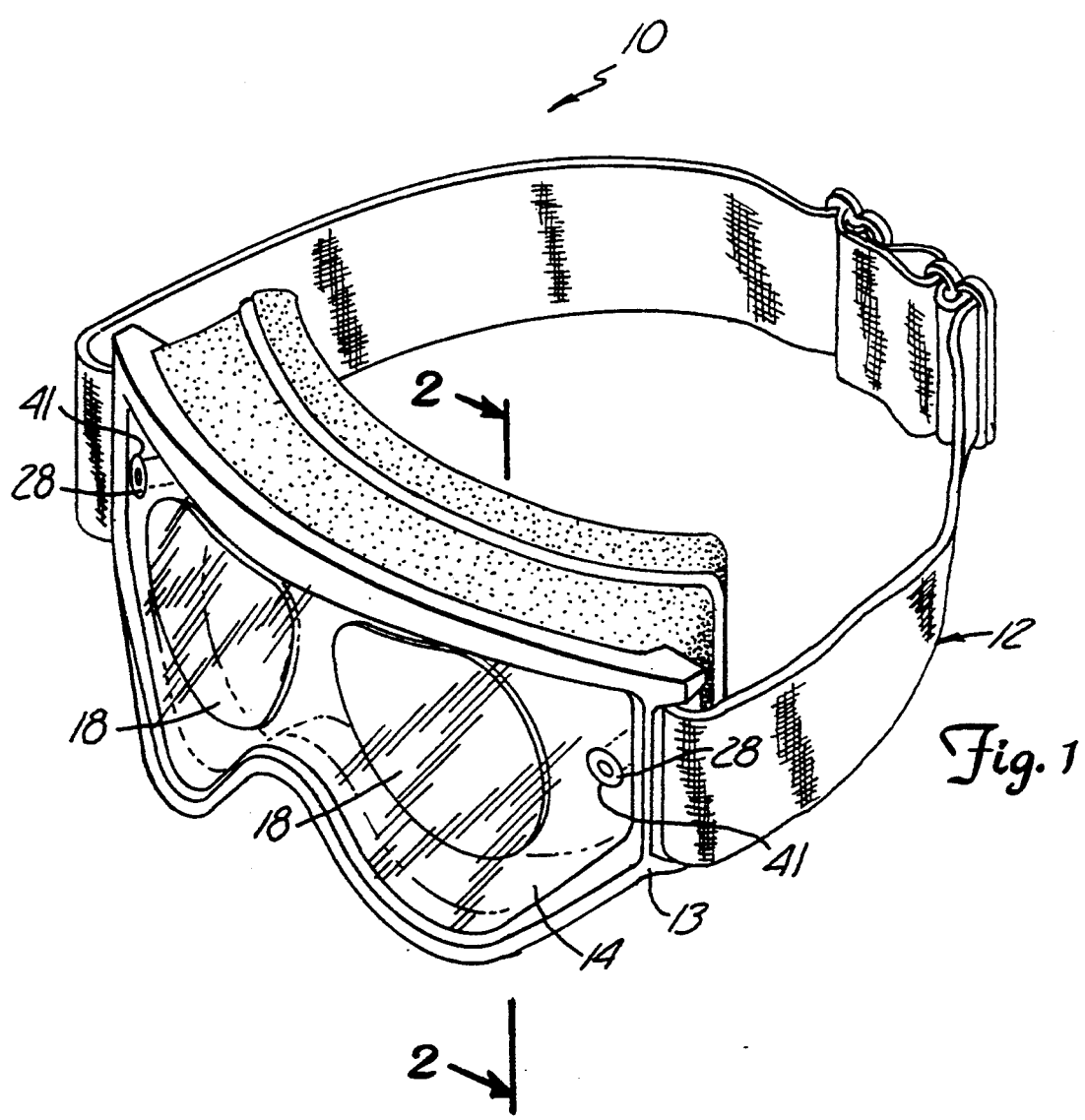
FIG. 1 is a perspective view of a protective goggles assembly of the present invention.
Figure 2:
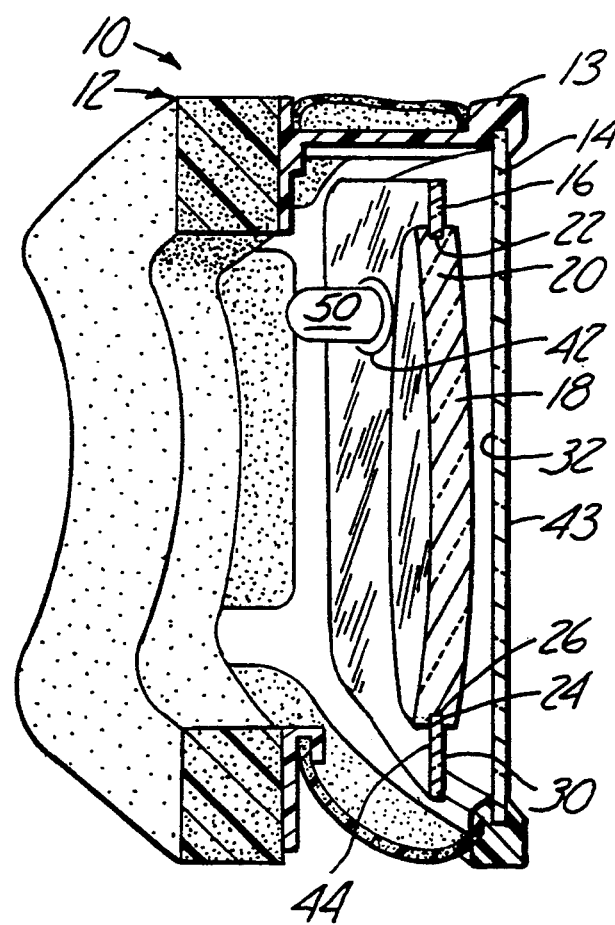
FIG. 2 is a sectional view of the protective goggles assembly taken along the line 2—2 of FIG. 1.

A protective goggles assembly 10 of the present invention is shown in FIGS. 1. The protective goggles assembly 10, which is shown in more detail in FIG. 2, comprises a pair of goggles 12 having a frame 13 mounting an outer lens 14 and an inner lens 16. A pair of corrective lenses 18 are mounted in the inner lens 16. The goggles 12 can be any one of a variety of types including motocross, ski or industrial safety goggles and are preferably of a type in which the outer lens 14 can be removed from the frame 13. The inner lens 16 comprises a flat, clear polycarbonate such as thin gauge Lexan and is flexible so that it can be easily fit into the goggles 12.

Two openings 20, each having a size roughly equivalent to that of one of the corrective lens 18, are formed in the inner lens 16 while a groove 22 is formed in an outer edge 24 of each corrective lens 18. Each corrective lens 18 is press-fitted into one of the openings 20 in the inner lens 16 such that an inner edge 26 of the inner lens 16 around each opening 20 rests in the groove 22 of the corresponding corrective lens 18. The corrective lenses 18 are thus held firmly in place in the inner lens 16.

The corrective lenses 18, which are ground to the prescription of the user, can be removed from the inner lens 16 by applying pressure to the lenses 18 until they snap out of the openings 20. This allows for the replacement of the corrective lenses 18 in the event that they becoming damaged or that the prescription must be changed.

Figure 3:
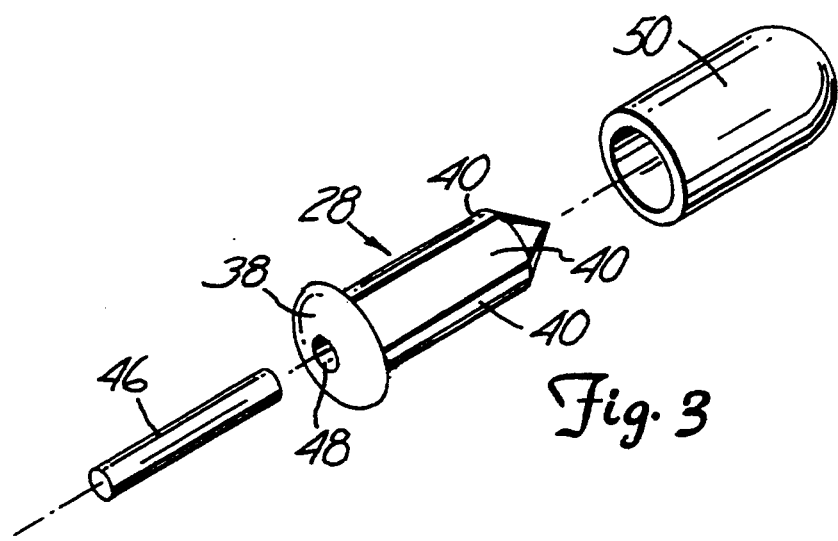
FIG. 3 is an exploded perspective view of a portion of the protective goggles assembly.

A pair of pegs 28 are used hold the inner lens 16 generally parallel to and spaced from the outer lens 14 such that a first side 30 of the inner lens 16 faces an inner surface 32 of the outer lens 14. The pegs 28, which are shown in more detail in FIG. 3, are fabricated from plastic and each has a head 38 at one end from which extends a plurality of flexible legs 40. Each peg 28 is inserted through an outer fastening hole 41 in the outer lens 14 and a corresponding one of a plurality of inner fastening holes 42 in the inner lens 16 such that the head 38 of the peg 28 rests against an outer surface 43 of the outer lens 14 and the flexible legs 40 extend through both the outer lens 14 and the inner lens 16.

The flexible legs 40 must be pressed together to enable the pegs 28 to fit through the outer and inner fastening holes 41,42. Once through the outer and inner fastening holes 41,42, the ends of the flexible legs 40 move apart and prevent the peg 28 from sliding back through the holes 41,42. A pin 46 is inserted into a bore 48 in the center of the head 38 of each peg 28 and extends substantially the entire length of the peg 28 to hold the flexible legs 40 spaced from each other. A cap 50 is placed over the ends of the flexible legs 40 and the pin 46.

The mounting of the corrective lenses 18 in the inner lens 16 by press-fitting the corrective lenses 18 into the openings 20 cut in the inner lens 16 has many advantages. A first advantage is that it enables a variety of sizes and shapes of corrective lenses to be mounted in the goggles 12. A second advantage is that the corrective lenses 18 can be easily replaced by corrective lenses ground to a different prescription, enabling more than one person to use a single protective goggles assembly 10. Further, the press-fit mounting prevents the corrective lenses 18 from being jarred out of alignment when the goggles 12 experience a shock during use.

The inner lens 16 is shown as attached to the goggles 12 and held spaced from the outer lens 14 by a pair of pegs 28 which extend through both the outer and inner lenses 14,16. However, the inner lens 16 can be attached to the goggles 12 in a variety of ways and can be mounted in the goggles 12 by attaching it to the frame 13 as well as to the outer lens 14. The inner lens 16 also is shown as a flat, clear polycarbonate. However, it can be fabricated from a variety of materials and can be tinted to aid in reducing glare caused by the sun or other bright objects.

Figure 4:
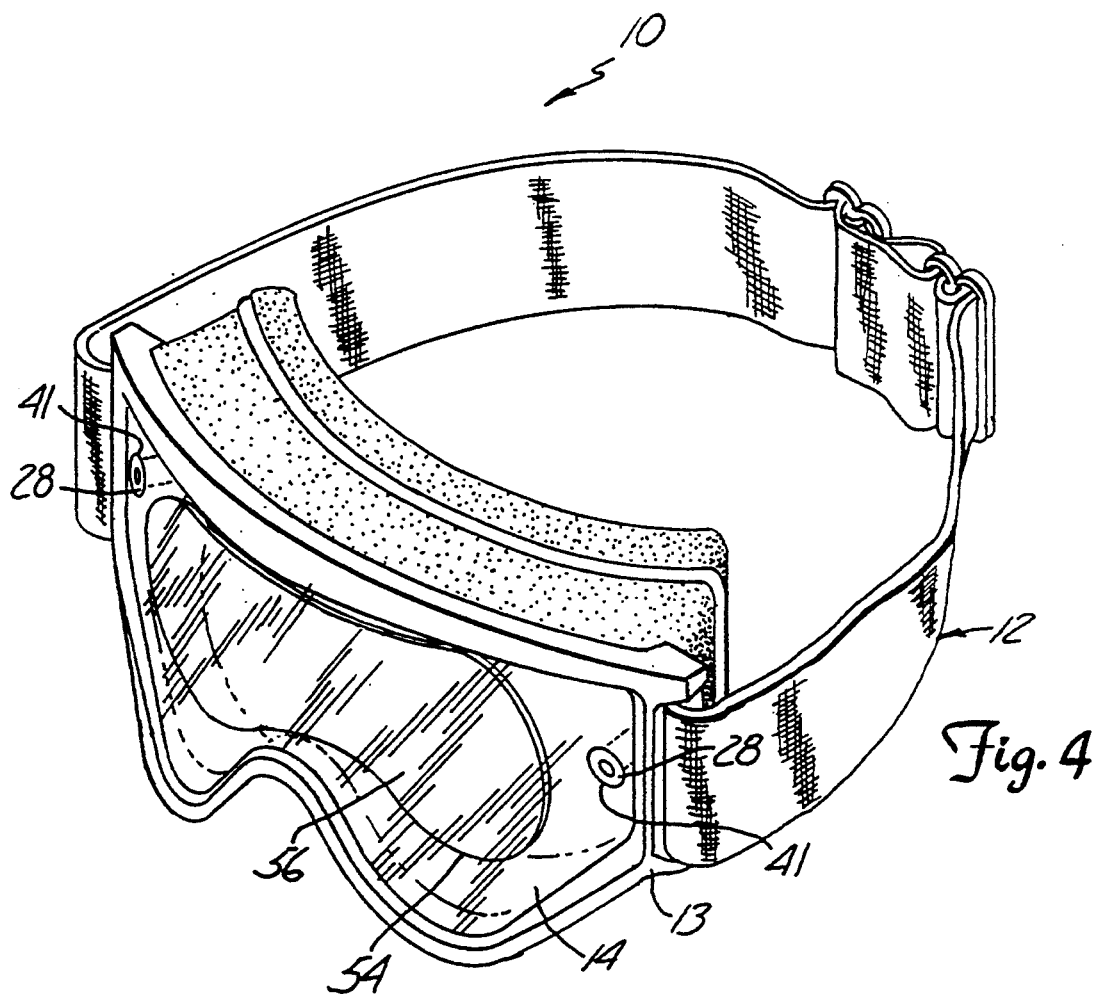
FIG. 4 is a perspective view of a modified form of the protective goggles assembly of the present invention.

While two corrective lenses 18 are mounted in two openings 20 in the inner lens 16 as shown, it is also possible to form a single opening 54 in the inner lens 16 in which is mounted a single corrective lens 56, as shown in FIG. 4. Additionally, the inner lens 16 itself can be cut in a variety of shapes, enabling it to be mounted in a variety of types of goggles 12.

By holding the corrective lenses 18 in the inner lens 16 behind the outer lens 14, the corrective lenses 18 are prevented from becoming scratched during use. In addition, the use of multiple inner fastening holes 42 in the inner lens 16 allows the inner lens 16 to be mounted in a number of positions relative to the outer lens 14. Finally, the inner lens 16 holding the corrective lenses 18 can be easily removed by removing the pegs 28, permitting the goggles 12 to be used by someone with unimpaired vision.

Although the present invention has been described with reference to preferred embodiments, workers skilled in the art will recognize that changes may be made in form and detail without departing from the spirit and scope of the invention.

What is claimed is:

1. A goggles assembly capable of having corrective lenses mounted therein, the goggles assembly comprising:
   goggles having an outer lens;
   a flexible lens holder having two lens openings formed therein, wherein the lens holder is flat when free of deforming forces and can be fixed to fit into the goggles;
   a pair of corrective lenses mounted in the lens openings of the lens holder, and an attachment holder for attaching the lens holder to the goggles.

2. The goggles assembly of claim 1 wherein a groove is formed in an outer edge of each corrective lens and each corrective lens is inserted in one of the lens openings such that a portion of the lens holder rests in the groove of the corrective lens.

3. The goggles assembly of claim 1 wherein the attachment holder comprises a fastener.

4. The goggles assembly of claim 1 wherein the attachment holder comprises a groove in the goggles capable of receiving an outer edge of the lens holder.

5. The goggles assembly of claim 3 wherein the fastener comprises a pair of pegs, each of which is inserted through a mounting hole in the outer lens of the goggles and a corresponding hole in the lens holder.

6. The goggles assembly of claim 5 wherein the lens holder is held substantially spaced from the outer lens.

7. The goggles assembly of claim 5 wherein each peg is held in place by a pin which is inserted into the peg and a cap covers a first end of each peg.

8. The goggles assembly of claim 1 wherein the lens holder comprises a polycarbonate.

9. The goggles assembly of claim 2 wherein the lens holder is held substantially spaced from the outer lens.

10. A goggles assembly capable of having a corrective lens mounted therein, the goggles assembly comprising:
    goggles having an outer lens;
    a flexible lens holder having a single lens opening formed therein, wherein the lens holder is flat when free of deforming forces and can be flexed to fit into the goggles;
    a corrective lens mounted in the lens opening of the lens holder; and
    an attachment holder for attaching the lens holder to the goggles.

11. The goggles assembly of claim 10 wherein a groove is formed in an outer edge of the corrective lens and the corrective lens is inserted in the lens opening such that a portion of the lens holder rests in the groove.

12. The goggles assembly of claim 10 wherein the attachment holder comprises a fastener.

13. The goggles assembly of claim 10 wherein the attachment holder comprises a groove in the goggles capable of receiving an outer edge of the lens holder.

14. The goggles assembly of claim 12 wherein the fastener comprises a pair of pegs, each of which is inserted through a mounting hole in the outer lens of the goggles and a corresponding hole in the lens holder.

15. The goggles assembly of claim 10 wherein the lens holder comprises a polycarbonate.

16. A goggles assembly capable of having corrective lenses mounted therein, the goggles assembly comprising:
    goggles having a frame and an outer lens;
    a flexible lens holder having two lens openings formed therein, wherein the lens holder is flat when free of deforming forces and can be flexed to curve in the same direction as the outer lens of the goggles;
    a pair of corrective lenses mounted in the lens openings of the lens holder; and
    an attachment holder for attaching the lens holder to the goggles.

* * * * *

UNITED STATES PATENT AND TRADEMARK OFFICE
CERTIFICATE OF CORRECTION

PATENT NO. : 5,371,555
DATED : December 6, 1994
INVENTOR(S) : RANDY NAGEL

It is certified that error appears in the above-indentified patent and that said Letters Patent is hereby corrected as shown below:

Col. 3, line 53, delete "fixed", insert --flexed--

Signed and Sealed this

Twenty-fifth Day of April, 1995

Attest:

BRUCE LEHMAN

Attesting Officer     Commissioner of Patents and Trademarks